United States Patent [19]

Esposito

[11] Patent Number: 4,723,952
[45] Date of Patent: Feb. 9, 1988

[54] OSTOMY DEVICES AND THEIR METHOD OF USE

[76] Inventor: Thomas Esposito, 1086 Benz St., Cincinnati, Ohio 45238

[21] Appl. No.: 829,479

[22] Filed: Feb. 13, 1986

Related U.S. Application Data

[63] Continuation-in-part of Ser. No. 705,358, Feb. 25, 1985, abandoned.

[51] Int. Cl.$^4$ ............................................. A61F 5/44
[52] U.S. Cl. ................................................... 604/338
[58] Field of Search ....................... 604/277, 332–345

[56] References Cited

U.S. PATENT DOCUMENTS

| | | | |
|---|---|---|---|
| 2,423,060 | 6/1947 | Zaro | 604/345 |
| 2,536,036 | 1/1951 | Cloninger | 604/332 |
| 2,684,676 | 7/1954 | Perry | 604/344 |
| 2,784,718 | 3/1957 | Fenton | 604/343 |
| 2,837,094 | 6/1958 | Cowles | 604/338 |
| 3,043,306 | 7/1962 | Hergatt et al. | 604/342 |
| 3,074,404 | 1/1963 | Robinson | 604/338 |
| 3,447,790 | 1/1971 | Hauser | 604/342 |
| 3,856,011 | 12/1974 | Blanchard | 604/343 |
| 3,897,781 | 8/1975 | Marsan | 604/338 |

Primary Examiner—C. Fred Rosenbaum
Assistant Examiner—J. L. Kruter
Attorney, Agent, or Firm—Edmund S. Lee, III

[57] ABSTRACT

An ostomy device is disclosed which comprises a simple, rigid frame having an opening which is registered with the stoma of an ostomate and secured on his torso by an elastic belt. The tension of the belt cause the frame to press into the user's flesh and thus stabilize the peristomal region within the confines of the frame opening. The peristomal region is given sufficient firmness to insure secure attachment of an adhesive sheet of a waste management adjunct. This frame is also employed in a method which obviates the need for a collection container for body wastes. In this method, a protective sheet may be adhered to the peristomal skin, with an opening registered with the stoma. A absorbent pad is held against the stoma by the frame as it stabilizes the peristomal region. The solid matter is then periodically removed by replacement of the pad. For use with a sanitary wafer which is adhered to the torso and has a flange on which a collection container is detachably mounted, a broader based stabilization is provided through the provision of a relatively rigid planar portion, spanning the inner end of the frame opening. This planar portion may be provided by a separate insert or formed integrally with the frame. The planar portion concentrates stabilization to the periphery of the stoma where the adhesive sheet portion extends to an opening which is registered with the stoma. The wafer flange projects through a central opening in the planar portion to permit mounting of the collection bag.

14 Claims, 16 Drawing Figures

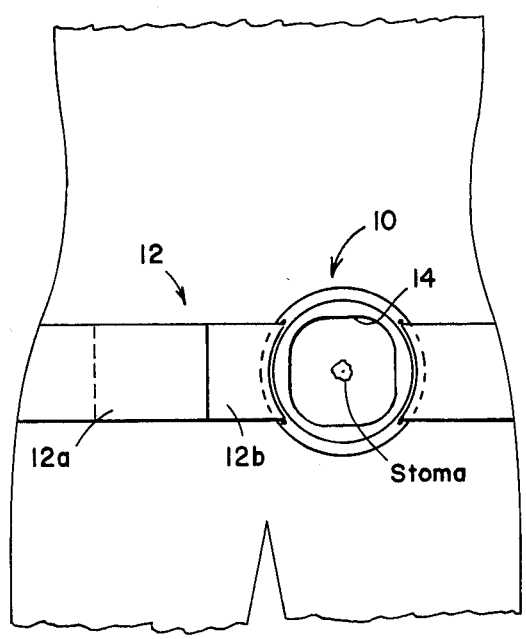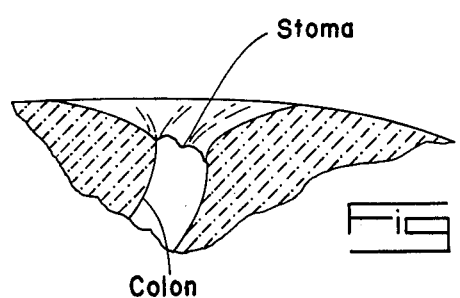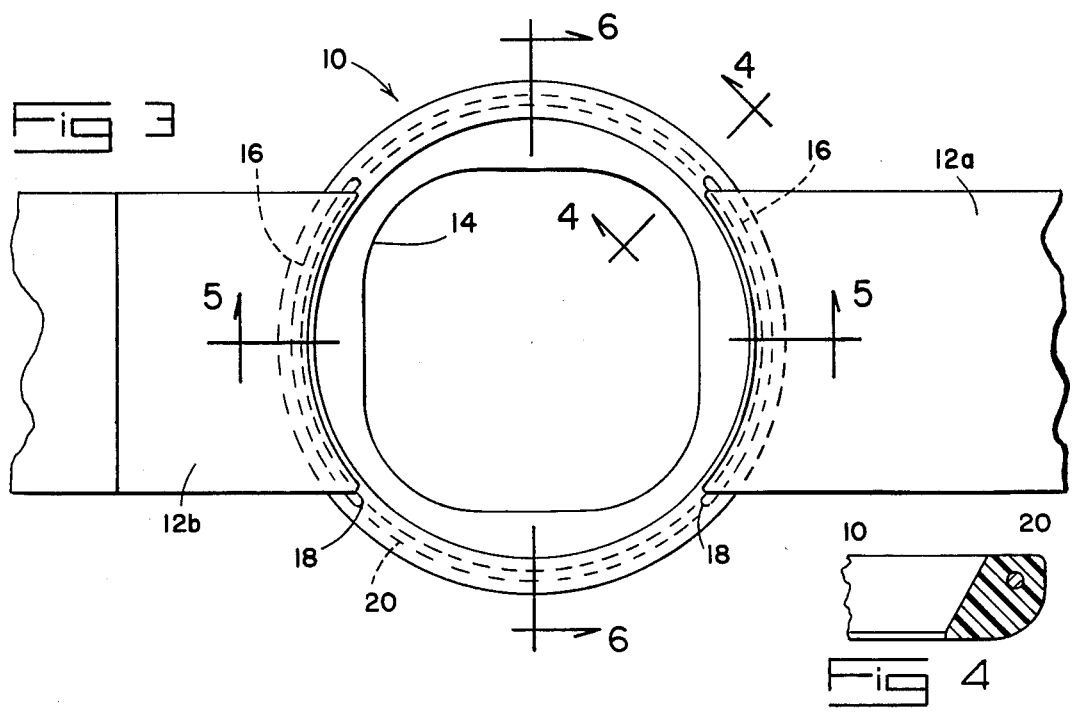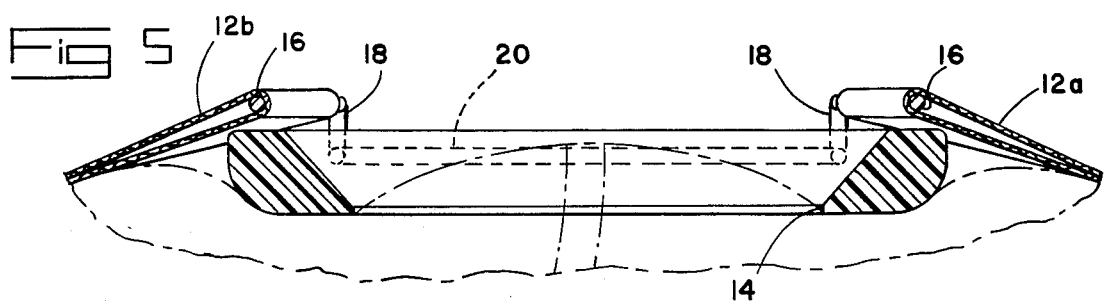

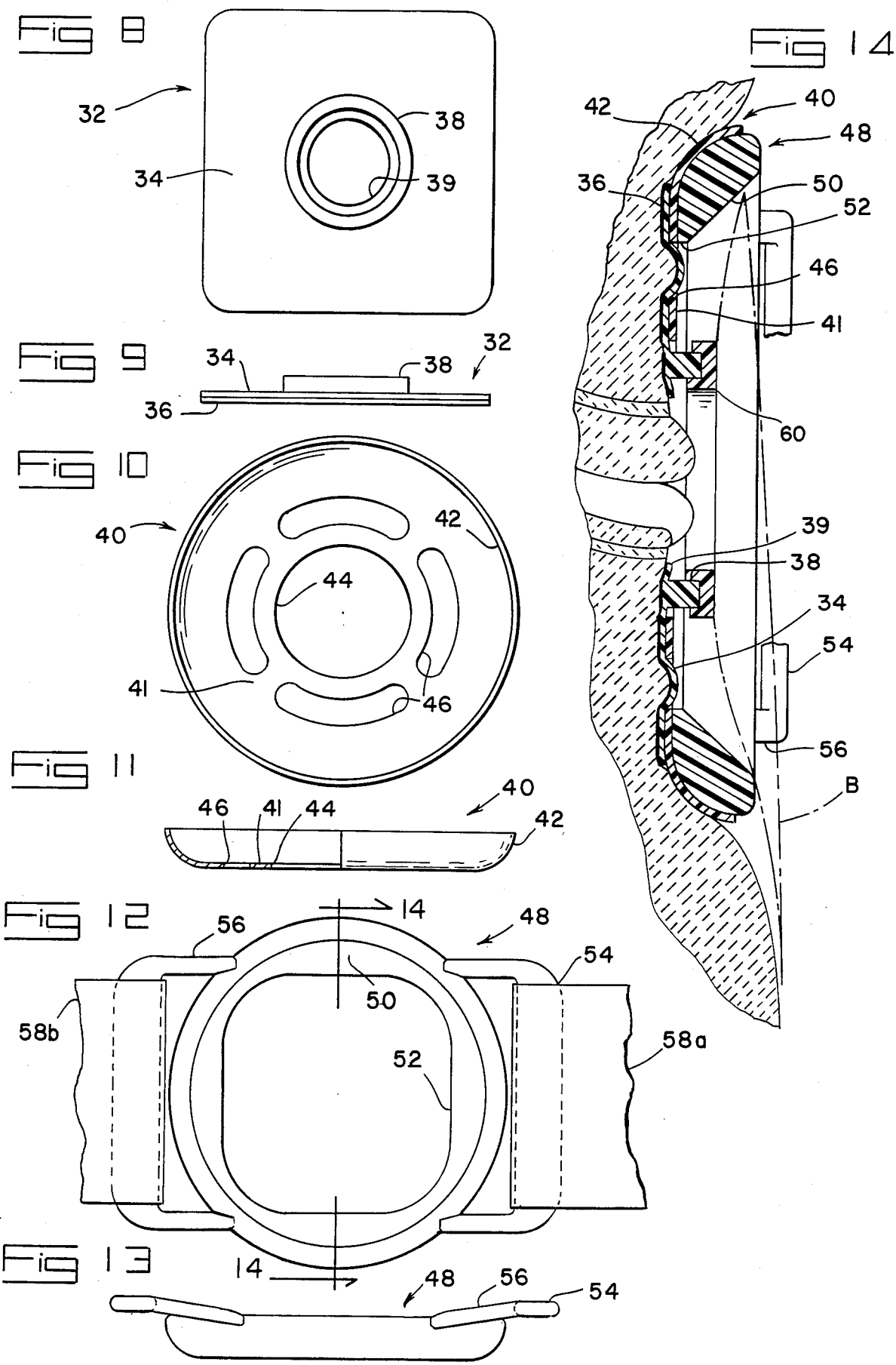

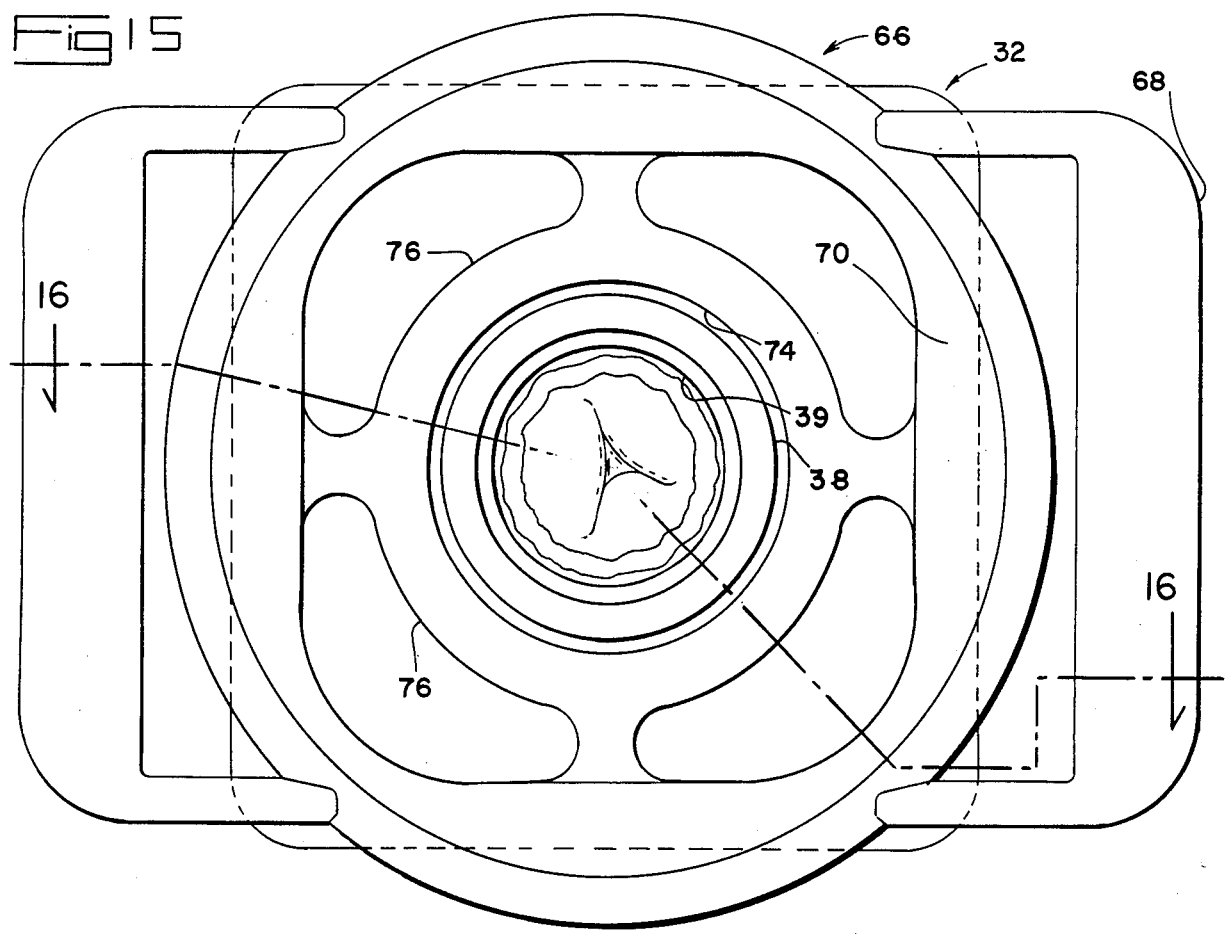
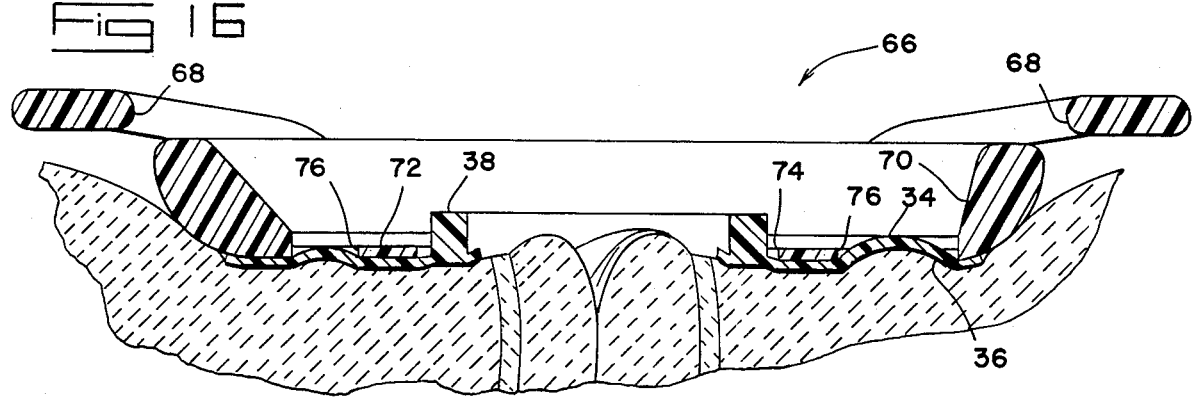

OSTOMY DEVICES AND THEIR METHOD OF USE

This application is a continuation-in-part of application Ser. No. 705,358, filed Feb. 25, 1985, now abandoned.

The present invention relates to improvements in the management of body wastes by ostomates, i.e., persons who have had a colostomy, urostomy or similar operation whereby waste is diverted for discharge through a surgically created opening, or stoma.

For several decades surgical procedures have been available for the excision of malignant portions of the intestinal tract. This, then entails creation of an an artificial opening to which the remaining, healthy portion of the intestine is attached to permit the discharge of body wastes. Such artificial openings, or stomas, are usually located on the front of a person's torso in the region of the abdomen. These procedures are known as colostomies, colectostomies and ileostomies, reflecting the various degrees to which the intestinal tract has been removed. A similar procedure is employed where the urinary tract is diseased. The ureter, in such case, is then connected to an artifical opening or stoma.

The obvious problem is to collect and contain the body wastes discharged from the stoma. This has involved the use of a container which in then emptied from time to time, or, in the more usual case simply replaced by a fresh container. While there are different problems unique to the several procedures, the basic difficulty is in providing a seal between the stoma and the the container.

It is also to be pointed out that there is no bodily control of discharge of the waste. The intestinal tract, for example, has a peristaltic, involuntary muscular movement, i.e., a wavelike motion of the intestine, which forces the feces in a discharge direction to the stoma. Similarly, flow through the ureter is continual and uninterrupted An essential requirement for an ostomy device is to accommodate normal activities, including athletic exercise, of the the ostomate, all of which involves bending of the torso and a resulting tendency to cause a folding or creasing of the body area where the stoma has been created. This is one of the factors which make obtaining an effective seal with the container difficult.

While a stoma may be generally characterized as a circular orifice, the stoma of each ostomate is unique. many are irregular to a greater or lesser degree, and may be sunken or protruding and have wrinkles radiating into the peristomal skin. These factors likewise contribute to the difficulties in obtaining an effective seal between the stoma and the container employed to collect waste.

The importance of an effective seal is vital. It is obvious that leakage of body wastes in undesirable, if not intolerable. Beyond this, the seal needs to be effective to prevent body wastes from contacting the peristomal skin. Feces, containing digestive juices, can literally eat the skin. The resulting lesions, in extreme cases could even be life threatening.

Ostomy devices came into being essentially at the inception of the surgical procedures, i.e., they have existed for many years. They have taken many forms and approaches to obtaining the desired seal between a collection container and the stoma, as is reflected both in the patent literature and in the present commercial market.

The effectiveness of these devices is limited. Many are not suited to the needs of an ostomate with a sunken or wrinkled stoma. Others are unduly complicated or expensive, for example one type device employs a sealing member custom-molded to the configuration of the individual's stoma and peristomal skin area.

As a general characterization, earlier forms of ostomy devices were predicated on the use of a rigid member which was intended to form a seal with the ostomate's skin surface peripherally of and spaced outwardly of the stoma. Such devices were pressed inwardly by belt means to provide a sealing pressure for the device. While the seal obtained could be effective in preventing leakage, the peripheral skin surface was constantly exposed to body wastes with result irritation from body wastes.

More recently, with the development of improved adhesives, ostomy devices have been based on an adhesive seal approach. A highly effective form of this approach is based on the use of what is termed a santiary wafer. This wafer comprises an adhesive sheet which adheres to the peristomal skin, with an opening therein permitting discharge of waste through the sheet. A circular flange projects outwardly from the sheet to provide for the detachable mounting of a collection container, or bag, into which body wastes are directed, from the stoma.

Nonetheless, the useful life of the sanitary wafers, as well as other devices using and adhesive seal approach, is quite limited, requiring frequent replacement of the device, usually on a daily basis, or more often.

Accordingly the broad object of the present invention is to alleviate the waste disposal problems experienced by ostomates.

A more specific object of the invention is to extend the usefulness and effectiveness of adhesive seals between a stoma and a collection container.

Another, more specific object of the invention is to eliminate, at least for a significant period of time, the need for a collection container.

A further object of the invention is to attain the above ends in a simple and economical fashion having applicability to virtually all types of stomas.

The objects of the present invention are attained through a device which stabilizes the stoma and peristomal region of the ostomate.

The stabilization obtained isolates the peristomal flesh and underlying body portions, from the surrounding portions of the torso and also gives it a firmness. These characteristics of stabilization enhance the effectiveness of body waste management adjuncts, such as the referenced sanitary wafer, as well as permitting some ostomates to dispense entirely with the need for a collection container.

While a limited number of prior ostomy devices have, in fact, stabilized the peristomal region, there has been no appreciation of the full potential of such stabilization in overcoming the waste disposal problems of the ostomate, as herein taught.

Thus the present invention embodies a simple, rigid frame in combination with a belt. The frame has a central opening which the ostomate registers with his stoma. The belt is then tightened about his torso. In so doing the frame is drawn into the flesh and the stoma and peristomal region is thus stabilized.

The device of the present invention is unobstructed, outwardly of the frame opening to provide manual access to the stabilized peristomal region. The stabilized peristomal region then has sufficient rigidity, or firmness, to permit secure attachment of an adhesive sealing sheet of the type commercially available for attaching a collection container, or a mounting device for a collection container, pursuant to the method aspects of the invention.

A further aspect of the present invention is found in a method employing this frame. For colostomates, an absorbent pad is placed over the peristomal region and the frame then secured to stabilize the peristomal region. While feces will be discharged by peristaltic action, the liquid content will be absorbed by the pad and the feces will solidify. The ostomate's sense of touch will alert him when there is a buildup of feces sufficient to require its disposal and replacement of the pad. Such disposal intervals will be in the order of several hours. Thus the ostomates bodily elimination function more nearly approaches that of the ordinary person, requiring no special collection containers. This method is predicated on the ostomate's ability to minimize liquid content of the feces through dietary control.

In other method aspects, the frame may first be used to stabilize the peristomal region and then an adhesive, protective sheet applied to the stabilized peristomal skin. This sheet has an opening which is registered with the stoma. The frame is then temporarily removed and an absorbent pad inserted to overlie the the protective sheet. The frame is remounted to hold the pad in place as above described. A protective sheet may also be inserted to overlie the absorbent pad to prevent moisture from penetrating to the ostomates clothing.

Structural features of the invention relating to the frame are found in the relationship between the span of its central opening and the nominal diameter of the stoma, preferably two to four times, and the thickness of the frame relative to the span of the opening preferably being 15 to 25% of the span. These features combine to provide manual access to the stoma, while causing a minimum protrusion of the ostomate's clothing. The preferred provision of a blunt edge at the inner end of the frame opening, avoids discomfort when the device is worn.

The inner end of the frame opening is preferably formed as an "rounded square" to resist displace of the device relative to the ostomate's torso.

Further features of the invention are specifically directed to enhancing the effectiveness of the referenced sanitary wafers which comprise a flexible, impervious sheet having a layer of adhesive on its inner surface. The sheet also has a flange projecting from its upper surface, on which a waste collection container may be mounted. An opening approximating the outline of the ostomates stoma is formed within the flange and approaches the inner diameter thereof.

In one version of the invention, an insert is employed to further stabilize the peristomal region and concentrate the stabilization closely adjacent the stoma opening of the protective sheet. The insert has a relatively thin planar portion which spans the insert opening. A central opening in this planar opening has a diameter approximating, but somewhat larger than the outer diameter of the water flange and is telescoped thereover.

This provides a high effective stabilization of the peristomal region immediately adjacent the periphery of the stoma opening in the protective sheet. The effectiveness of the adhesive seal at this critical point is thus greatly enhanced, extending the useful life of the sanitary wafer several fold.

In another version of the invention this thin planar section is integrally formed with the ostomate frame.

One of the structural features of devices for the sanitary wafer is the provision of openings in the planar section, within the outline of the frame opening, outwardly of the flange opening, through which the ostomate's flesh protrudes to further minimize relative movement between the device and the santiary wafer and the ostomate's torso.

The present invention represents a distinctly new approach to body waste management. It is based on a rigid device, the function of which is not to form a seal with the skin surface of an ostomate, as other rigid devices have done, but instead to stabilize the peristomal region and thereby to enhance the effectiveness of adhesive seals of body waste management adjuncts, or to enable the ostomate to dispense with a collection container.

The above and other related objects and features of the invention will be apparent from a reading of the following disclosure, making reference to the accompanying drawing and the novelty thereof pointed out in the appended claims.

In the drawings:

FIG. 1 illustrates the front of the torso of an ostomate, with an ostomy device embodying the present invention, secured in place;

FIG. 2 is horizontal section illustrating a typical stoma;

FIG. 3 is a front view, on an enlarged scale of the ostomy device seen in FIG. 1;

FIG. 4 is a section, on a further enlarged scale, taken on line 4—4 in FIG. 3;

FIG. 5 is a section, on the same further enlarged scale, taken on line 5—5 in FIG. 3, with the stabilized peristomal region shown in broken lines;

FIG. 8 is a plan view of an adhesive wafer to which a disposal bag is attached;

FIG. 9 is an elevation of the wafer seen in FIG. 8;

FIG. 10 is a plan view of an insert used in combination with the present ostomy device;

FIG. 11 is an elevation, partly in section, of the insert seen in FIG. 10,

FIG. 12 is a plan view of an alternate embodiment of the present ostomy device;

FIG. 13 is an elevation of the ostomy device seen in FIG. 12;

FIG. 14 is a vertical section, on an enlarged scale, of the wafer, insert and ostomy device of FIGS. 8-13 secured in place on the body of an ostomate;

FIG. 15 is a plan view of a further embodiment of the present ostomy device secured on the body of an ostomate, illustrating its relationship to the wafer of FIGS. 8 and 9; and FIG. 16 is a section taken generally on line 16—16 in FIG. 15.

Figure 6:
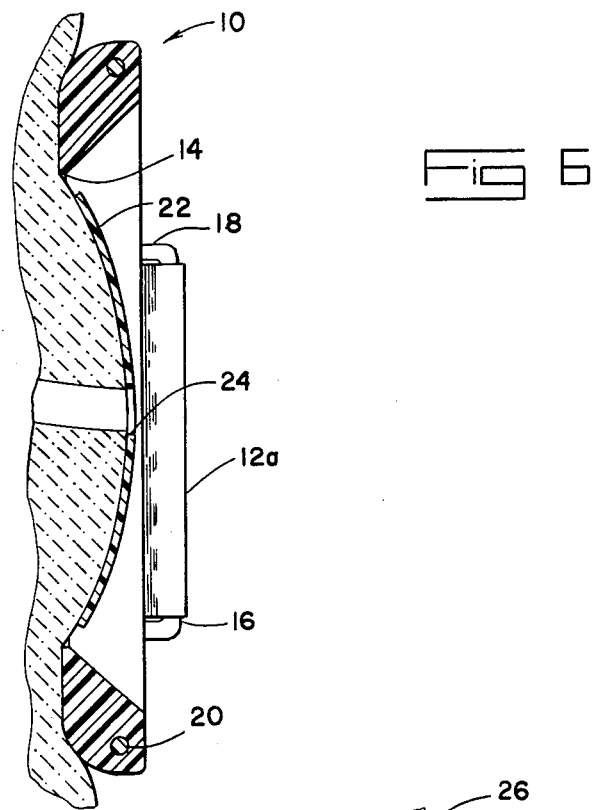
FIGS. 6 and 7 are sections, also on said further enlarged scale, taken on line 6—6 in FIG. 3, illustrating method aspects of the invention.

Before giving a detailed description of the specific embodiments, herein disclosed, a brief discussion of stomas will be had. Many factors have a bearing on the physical configuration of a stoma. As indicated above, medical factors determine what portion of the intestinal tract must be removed. This, plus the stature and age of a person will control the diameter of the portion of the intestine (used generically to include a colon, or bowel), which is to be joined to the abdomen in forming a stoma. Stoma diameters, measured from the outer wall of the intestine, generally range from 1 to 1⅜ inches, though stoma diameters outside of this range are not unknown.

The intestine itself comprises a compositely formed tubular structure comprising an outer wall and a flesh-like inner lining. The outer wall of the intestine is sutured to the muscle wall of the abdomen, with the terminal end of the intestine, ideally, flush with the skin surface of the abdomen, sutures also being provided at this juncture. Unfortunately, this ideal condition is often not obtained and the stoma is retracted, or sunken beneath the level of the abdomen, or the intestine may extend outward causing a protruding stoma, projecting above the normal level of the skin.

The outer wall of the intestine is essentially inexpansible and, thus, at the stoma, its diameter, for practical purposes, is a constant. The fleshlike inner lining of the intestine is expansible and compressible, within the outer wall, to accommodate feces which advance therethrough by reason of peristaltic action.

FIGS. 1, 2, 5–7, 14, 15 and 17 variously illustrate stomas as herein described. The inner walls of the stoma, in the absence of feces (as in FIG. 7), expand, or collapse inwardly, so that there is little or no open passageway extending through the intestine.

The skin surface surrounding the stoma can be irritated and even ulcerated as a result of exposure to feces and digestive juices which are exuded from the stoma. Adhesively applied sheets are available to protect the peristomal skin surface from this source of irritation. It is an accepted practice for an ostomate to obtain a punch which is accurately configured to the outline of his stoma. Such a punch is employed to form an opening in the the protective sheet which is then registered with the stoma, so that essentially no peristomal skin surface is exposed to feces. It is to be noted that the stoma is seldom of a truly circular outline and can be both irregular, or jagged, as well as somewhat elliptical, hence reference is made herein to the nominal diameter of the stoma.

The devices of the present invention have as their primary function, the stabilization of the peristomal region, both the skin and underlying flesh, so that the effectiveness of the adhesive for the protective sheet will be enhanced and preserved. The stabilization provided thus prevents, for prolonged periods, leakage of feces, or digestive juices, between the protective sheet and the peristomal skin surface. Such stabilization also enables feces management without the need of a collection container, or even a protective sheet.

Referencing FIG. 1, it will be seen that the illustrated ostomy device of the present invention is extremely simple, comprising only a frame 10 and a belt 12 which holds it in registered relation with the stoma of an ostomate.

The frame 10 in preferably of circular outline with an opening 14 which has a "rounded square" outline, at its inner end, which blends to a circular outline at its outer end. The surface of the frame opening 14 is preferably beveled outwardly its inner end which is defined by a small, vertical flat at a lip defined by the inner end of opening and the inner surface of the frame which is to be pressed against the flesh of the ostomate. Peripherally of the inner end of the opening 14, the inner surface initially extends outwardly, generally normal to the opening 14, and then curves outwardly to form the circular side surface of the frame. The lip thus causes only a minimum pressure and discomfort when the frame is pressed against the flesh of the ostomate, as will later appear.

While dimensions will vary for ostomates of different stature and build, as well as for stoma location, it has been found that a frame diameter of approximately 4½ inches and an opening of approximately 3 inches, with a thickness of ½ inch is preferred for approaching a device universally applicable to more than 90% of colostomates. Further these preferred dimensions provide a minimum restriction to the ostomate's activities, while achieving the waste disposal objectives of the present invention. A further function of these preferred dimensions is the comfort factor, i.e., the base of the frame is sufficiently wide that it does not exert an undue concentration of pressure, and yet the belt can be sufficiently tensioned to obtain the desired stabilization of the peristomal region. Thus further enhances the the comfort factor of the blunt lip at the inner end of the opening 14.

The belt 12 comprises two portions, 12a and 12b, respectively secured to opposite sides of the frame 10. Thus, wire bridges 16 are spaced from the outer surface of the frame 10 by posts 18. The ends of the belt portions 12a and 12b are looped respectively around the bridges 16 and secured to themselves to provide for attachment to the frame 10.

The free ends of the belt portions 12a and 12b are preferably provided with fastener strips strips so that these ends may be releasably secured to accommodate ostomates of varying girths in using the ostomy device. Hook and loop fasteners sold under the trademark Velcro are representative of the fasteners which may be used.

The primary physical characteristic of the frame is that it be rigid. Many materials would suffice, however, any of several resinous materials, often referred to as plastics, are preferred for their light weight and ease of fabrication, as by molding. In the same vein, the bridges may be formed of metal wire, with the posts 18 bent therefrom and then joined to internal reinforcements 20 embedded in the frame (see FIG. 4) as an uninterrupted ring, which reinforces the rigidity of the plastic device into which it is molded. A further preferred dimensional relationship is found in the distance of the top of the bridge from the lower surface of the frame. A distance of approximately ⅝ inch has been found highly effective in obtaining the desired stabilization with a tolerable belt tension and a minimal bulging of the clothing.

FIG. 2 illustrates a typical stoma of the the sunken type. The colon, at its point of attachment to the abdominal wall, forms The stoma. Because of the shortness of the colon, the peristomal region is drawn inwardly and wrinkled.

In use and in accordance with method aspects of the invention, the frame 10 is positioned on the torso of the ostomate, with the opening 14 registered with the user's stoma. The belt 12 is wrapped around the torso of the user and, after tightening, is secured by the Velcro fastenings. Preferably the belt 12 is fabricated of elastic material which permits the user to bend and otherwise indulge in activities which would tend to vary his girth, while maintaining a substantially uniform tension on the belt.

From FIG. 5, it will be seen that, when the frame 10 is thus tightened in place, the peristomal region is bulged outwardly bringing the stoma into the plane of the peristomal skin surface. The peristomal region is thus stabilized, with its surface in a defined position which remains virtually unchanged, regardless of the activities of the user. This stabilization is the result of inward pressure of the frame, which is, in turn, a function of the fact that the belt parts 12a and 12b are attached to the bridges 16, which are spaced outwardly of the inner surface of the frame. Thus it is possible to obtain an inward pressure without requiring an undue and uncomfortable tensioning of the belt when attaching the device. Comfort is also a consideration in the rounding of the outer periphery of the frame at its inner surface.

Stabilization of the peristomal region in this fashion serves two very important functions. First, the stoma is brought outwardly relative to the skin surface, so that it is no longer sunken, and also the wrinkles are stretched to a smooth surface. Secondly, the peristomal region is now firm. These factors enable a highly effective, adhesive seal to be obtained. A sealing sheet can be employed with an opening closely matching the outline of the stoma. Such an adhesive sheet can then be firmly adhered to the peristomal skin, by finger pressure which assures adhesion and prevention of feces, and more importantly the digestive juices in the feces, with the skin. Not only does this stabilization of the peristomal region assure greater initial adhesion and sealing of the skin from the feces, it also prevents a break down of the seal obtained.

To illustrate, one form of waste disposal system employs a sanitary wafer which comprises an adhesive sheet with a mounting flange on its outer surface. The sheet is secured to the peristomal region with an opening registered with the stoma. A disposable, flexible container is then mounted on the ring and replaced from time to time as it is filled with feces. (This type of disposal system is dealt with in greater detail, hereinafter, in connection with further embodiments of the invention.) Normally the adhesive sheet must be replaced after not more than seven days, and frequently at much shorter intervals to prevent leaking and/or skin irritation, as digestive juices seep under the sheet because of a breakdown of the adhesive. When this same device is attached with the peristomal region stabilized by the device of the present invention, replacement has not been required after usage for as long as 18 days.

It will be seen that the outward bevel of the frame opening 14 facilitates application of the adhesive sheet. The same consideration motivates the curvature of the bridges 16 so that they are displaced from the outline of the opening.

The illustrate "rounded square" configuration of the frame opening 14 serves to minimize any tendency of the frame to be displaced laterally relative to the body of the user. It also facilitates use of certain commercially available adhesive sheets used with waste containers, which have such configuration.

Again, an important point to note is that the outline of the frame opening is spaced laterally outwardly from the stoma and that the inward pressure of the inner surface of the frame, causes the peristomal region to bulge outwardly into the frame opening. This region is stablized in the sense that the skin surface configuration is relatively stable and isolated from the body portions outside the confines of the frame to the end that body movement, such as bending and twisting, which would otherwise cause flexing of the peristomal skin and relative movement between this skin portion and the protective sheet. Such relative movement is the cause of a breakdown in the effective of the attaching adhesive and resultant seepage of feces beneath the protective sheet.

Attention is now directed to further method aspects of the invention. Previously it has been an accepted concept that a waste receptacle must, at all times, be employed, due to peristalsis, which involuntary action, continuously tends to discharge feces from the stoma. With the stabilization of the peristomal region obtained by the frame previously described, it is now possible to dispense with the container, assuming that the ostomate, through dietary control, is able to maintain a minimal liquid content in the feces, this being a demonstrated capability.

Employing the frame 10, the peristomal region is first stabilized, as shown in FIG. 6, and a protective sheet 22 is adhesively applied to the peristomal skin within the outline of the frame opening 14. This protective sheet has a central opening 24 which is aligned with the stoma of the user.

Figure 7:
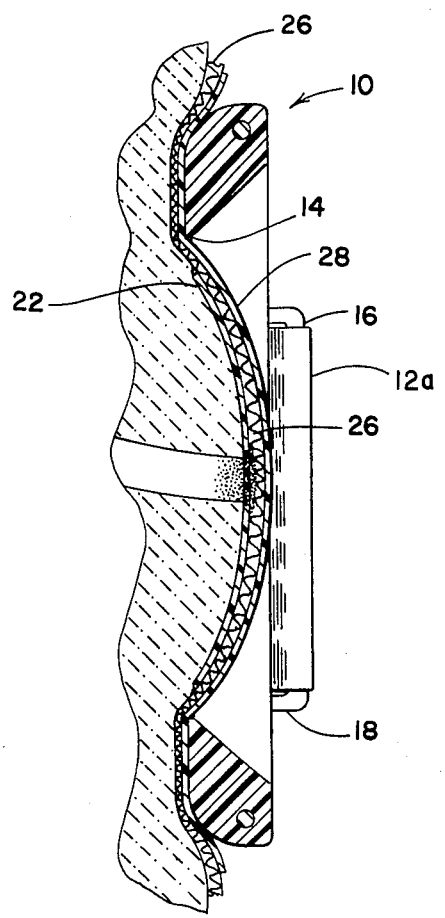

The belt 12 is then loosened and an absorbent pad 26 placed over the protective sheet 22. Also an outer moisture barrier sheet 28 overlies the absorbent pad 26. The sheet 28 has an outline greater than that of the frame 10. Thus when the frame is remounted, as shown in FIG. 7, the pad 26 is firmly held against the stoma as the peristomal region is again stabilized.

This system provides adequate waste disposal protection even where there is a relatively high liquid content in the feces. The sheet 22 protects the skin from the harmful affect of the digestive juices, while the barrier sheet 28 protects against moisture from seeping through to the user's clothing. With this system, it would also be possible to engage in water sports, and the like without feces contamination.

Where the liquid content of the feces is lower, even greater advantages can be obtained by using a barrier sheet 28 which is perforated. The rate of feces exudation is, generally, relatively slow. In fact, it will be sufficiently slow that the liquid will evaporate, through the perforations in the barrier sheet. However, the sheet still spaces the pad from the ostomate's clothing so protection is had in the event small amounts of moisture migrate to the outer surface of the absorbent pad.

This leads to the simplest method of all, where the liquid content of the feces is minimal. In such case, the barrier sheet 28 can be eliminated altogether. In fact, unless the ostomates skin is extremely sensitive to digestive juices, the skin protective sheet 22 can also be eliminated, because the rate of absorption and evaporation through the pad 26 is sufficient to prevent any substantial contact of the peristomal skin with digestive juices.

Many materials will suffice for the absorbent pad 26. A most economical expedient is simply to use an ordinary kitchen paper towel, folded into eight layers. Similarly, the barrier sheet 28 can be any common plastic film, such as are commonly found in kitchen use.

With the absorbent pad 22 held in place by the frame 10, the feces will tend to solidify as a solid, yet plastic plug in the terminal end of the colon, at the stoma, see FIG. 7. As the feces builds up, this plug will gradually protrude from the stoma. From experience, through the sense of feel, the ostomate can readily determine when feces buildup has reached a tolerable limit. At such time, the frame can be removed and the absorbent pad taken by the fingers and disposed of in a toilet, all without the fingers contacting the feces.

As was earlier indicated, this method is predicated on a relatively low liquid content in the feces. Dietary habits to obtain this end are well known and will also control feces volume. With proper controls, it is possible to go for 24 hours or more without requiring a change of the absorbent pad.

Again, the stabilization of the peristomal region, provided by the frame 10, is of significance in enabling this method of feces disposal. It enables the solidified feces to be readily removed, in addition to preserving the effectiveness of the adhesive for the protective sheet 22.

Reference is next made to FIGS. 8–14 for a description of the benefits of the present invention is connection with the previously referenced disposal system in which the protective sheet is in the form of a flanged, sanitary wafer to which a disposal bag is attached.

FIGS. 8 and 9 illustrate such a wafer, identified by reference character 32. Such wafers are commercially available. They comprise a generally rectangular, flexible sheet 34 of flexible, polymeric material, the lower, or inner surface of which is formed of a layer 36 (thicknesses are exaggerated in FIG. 9) of adhesive material permitting its attachment to the peristomal region of the the ostomate.

A circular flange 38, formed of relatively rigid polymeric material projects from the upper, or outer, surface of the flexible sheet 34. The sheet extends within the outline of the inner diameter of the flange 38 to an opening 40 through which the feces will pass. As will later appear, a feces disposal bag is then attached to this flange, after the wafer is attached to the peristomal region of the ostomate.

In further description of the wafer 32, it is to be recognized, that the generally circular stomas, vary in diameter from one individual to another. In order to essentially eliminate feces leakage along the inner surface of the sheet 34, it is essential that inner diameter of the flange 38 and the underlying adhesive layer 36 closely approximate the diameter of the individual stoma, or be only minimally larger. Thus the wafers are available with incrementally variable flange diameters. The preferable practice is for an ostomate to have a circle cutter so that he can cut an opening 39 to custom fit the diameter of his stoma. In this fashion, the peristomal skin may be protected from feces irritation by a short lip line extension of the sheet 34 and more particularly by the adhesive layer, which also has a neutralizing effect on the acidic effects of the digestive juices.

Next, reference is made to FIGS. 10 and 11 for a brief description of an insert 40, preferably formed of relatively rigid polymeric material. The insert is formed with a planar central portion 41 and a curved outer flange 42. A central opening 44 has a diameter approximating, but greater than the outer diameter of the wafer flange 38. Additionally arcuate openings 46 are formed concentrically of the opening 44, for purposes which later appear.

Reference is now made to FIGS. 12 and 13 which illustrate an alternate ostomy frame 48, corresponding to the frame 10 described in FIGS. 1–5. The primary difference is that the frame 48 is an integral member, conveniently formed by molding.

Again a central opening 50 is provided within the circular outline of the frame. The surface of the opening 50 is angled outwardly from its inner end at lip 52, (see also FIG. 14). The same dimensions for the frame 48 and its opening 50, as given for the frame 10, would be preferred.

The frame 48 is adapted to be secured to the torso of an ostomate by a belt means in the same fashion as the frame 10. However, these means are attached to bridges 54 which are connected to the main body of the frame 10 by integrally molded legs 56, corresponding to the metal posts 18, previously described. Belt portions 58a and 58b are secured to the bridges 54, in correspondence with the belt portions 12a and 12b.

The frame 48 may be employed in the same fashion as the frame 10 to stabilize the peristomal region to facilitate attachment of various feces disposal systems, or for the management of feces disposal through the described method aspects of the invention.

However, the frame 48, or the frame 10, is also adapted to cooperate with the insert 40 to enhance the advantages of the sanitary wafer 32. In use, the wafer is first applied to the stomach of the ostomate. This can be done, in conventional fashion, by distension of the stomach muscles and pressing the adhesive layer against the surface of the skin, with the opening 39 registered with the stoma. Alternatively, the frame 48 can be used to temporarily stabilize the peristomal region, as previously described, to facilitate the mounting of the sanitary wafer 32.

After the wafer is in place, the insert 40 is manually pressed against the outer surface of the wafer 32, with the flange 38 projecting through the insert opening 44.

Next, the frame 48 is manually pressed against the insert 40, being centrally registered relative thereto by the curved flange 42 which mates with the outer curved surface of the frame. The frame is then secured to the ostomate's torso by tensioning the belt portions 58a and 58b and securing them together, as previously described.

The mounted positions of the wafer, insert and frame are illustrated, on an enlarged scale, in FIG. 14. FIG. 14 also illustrate a waste disposal bag B with which the wafer 32 is adapted to cooperate. The bag B may be formed of thin, flexible sheet material secured to an attachment ring 60 which telescopes onto the wafer flange 38. The flange 38 and ring 60 engage to provide a seal to prevent leakage of fecal matter between their mating surfaces on the inner diameter of the flange 38. Various refinements in configuration are available to enhance this sealing action.

Several features are to be noted from the mounted, or operative position of the waste management system as illustrated in FIG. 14, wherein the components are in the relative positions seen in FIGS. 8–13.

Again the peristomal region is stablized, which is a basic principle of the present invention. However, the stabilization achieved is with pressure exerted through the full extent of the planar portion 41 of the insert 40.

The inward pressure obtained as greater effectiveness in maintaining the effectiveness of the adhesive seal, but, because of the large area over which it is spread, unit pressure, or concentration is decreased, to the end of greater comfort for the ostomate.

As with the frame 10, the lining of the intestine is also bulged out, which is again of particular importance in the case of sunken stomas. It is to be noted that the condition of the colon and its lining at the stoma is illustrated in FIG. 14 more graphically than in FIG. 5. This is to note that the colon, while generally circular in outline, is expansible. When feces are not present in the colon, (the condition illustrate in FIG. 14), the colon wall folds inwardly. In the stabilized condition of FIG. 14, the terminal portions of the colon wall bulge outwardly. This "budding" effect facilitates isolation of the irritating digestive juices from the ostomates skin, peripherally of the stoma. The manner of folding of this lining can vary greatly and what is shown in the drawings is merely representative.

It is also to be noted that this stoma "bud" is positively positioned to lie primarily within the flange 38 and ring 60 and well below the outer surface of the frame 48. Thus this "bud", which is highly sensitive, is extremely well protected from painful pressures and blows, even when the ostomate engages in strenuous activities.

When the belt means 58 a and b are tightened to draw the frame inwardly and stabilize the peristomal region, the wafer sheet 34 will be stretched, as permitted by the adhesive layer 36, to minimize, if not eliminate any wrinkles which would permit leakage of fecal material.

More importantly, there is a circular concentration of pressure to enhance the sealing effect of the adhesive layer 36, immediately at the periphery of the stoma. It will be noted that the edge of the insert opening is closely adjacent the flange 38. The flange 38, being relatively rigid, then provides an sealing force on the underling portion of the adhesive layer 36. Finally this inward sealing force is transmitted to the lip of the sheet material which extends to the opening 40 which is, preferably, custom cut to the outline of the stoma.

The openings 46 also contribute to the effectiveness of the seal obtained by the adhesive layer 36. As will be seen in Figure 14, the soft tissue of the stomach bulges into these openings. This creates further lines of pressure concentration which enhance the effectiveness of the seal obtained by the adhesive layer 36. Additionally, the multiple pressure concentration points, which are effective on the stomach tissue, minimze the possibility the frame, insert and wafer from shifting laterally, which, in turn, would degenerate the effectiveness of the seal and accelerate the possibility of leakage.

Another point to be noted is that the nested relationship between the frame 48 and insert 40 provides means for preventing lateral shifting between these elements.

Finally reference is again made to the pressure concentration immediately at the periphery of the stoma. When a disposal bag is attached to the flange 38, the ring 60 exerts an inward pressure which tends to displace the central portion of the wafer inwardly. Similarly, when the bag is removed, there is a tendency to pull the central portion of the wafer outwardly. Such movement causes a shearing action in the adhesive layer 36, outwardly of the opening 40, as the sheet 36 (and ring 38) are shifted outwardly, or actually pulled away from the skin in the case of bag removal. All of this tends to cause a degeneration of the adhesive layer and a breakdown in the effectiveness of the seal obtained. While the stabilization obtained by the present invention does not totally prevent such movement, it very significantly less than in the absence of such stabilization, as where the wafer is simply attached to the skin.

In summary, the broad based region of peristomal stabilization, here described, provides a highly effective sealing action, with a minimum of discomfort to the ostomate. The need to replace sanitary wafers is greatly reduced, a use life of seven days has, typically been extended to 30 days or more. It has the further advantage of a low profile which makes it virtually unnoticeable under normal clothing, as well as giving freedom of movement for essentially all physical activities.

The atlernate embodiment of the invention seen in FIGS. 15 and 16 combines the features of the insert 41 integrally into a frame and is customized for use with a sanitary wafer 32, as shown in FIGS. 8 and 9.

This frame, identified by reference character 66, is identical with the frame 48 in being of circular outline with bridges 68 to which elastic belt portions are attached to permit its being secured to the torso, as previously described. Likewise, a "rounded square" opening 70 is formed centrally of the frame.

An integrally formed, planar portion 72 extends across the bottom of the opening 70. A central opening 74 is provided in the planar portion 70. The planar portion is also provided with openings 76 the outer portions of which follow the outline of the "rounded square" opening 72 and the inner portions of which are generally concentric of the opening 74.

FIGS. 15 and 16 illustrate the frame 66 in its operative or functional relation with respect to a sanitary wafer 32 and the stoma of an ostomate. Stabilization of the peristomal region is essentially the same as described in connection with the frame 48 and insert 41, noting that the belt portions are omitted and the disposal bag has not been illustrated as it would be mounted on the flange 38. It will be seen that the openings 76 have a variable width so that there is a variation in the extent to which the stomch tissue protrudes therein, or therethrough. This feature further assures that the frame will not shift laterally and destroy the effectiveness of the adhesive layer 36.

The disclosure has been directed to devices and methods for colostomates and other intestinal ostomates, however, the present invention in many aspects, is also applicable to urostomates. Additionally variations from the specific teachings herein will occur to those skilled in the art which will provide equivalent benefits. The spirit and scope of the invention is, therefore, to be derived from the appended claims.

Having thus described the invention what is claimed as novel and desired to be secured by Letters Patent of the United States is:

1. A method of body waste management, for ostomates, through the use of a device comprising a relatively rigid frame having a central opening therein, which opening has a span substantially greater than the nominal diameter of the ostomate's stoma, and belt means attached to opposite sides of the frame, at points spaced from the inner surface thereof, said method comprising the steps of positioning said frame on the torso of the ostomate, with the opening thereof registered with the ostomate's stoma, securing the belt means about the ostomate's torso with sufficient tension to draw the frame inwardly and stabilize the ostomate's peristomal region disposed generally within the outline of said opening, and adhering a waster management adjunct to the skin surface of the ostomate, peripherally of the stoma and within the outline of the frame opening, said adjunct is in the form of a sanitary wafer comprising a flexible, impervious sheet having a layer of adhesive on its inner surface, said sheet also having a flange, projecting from its outer surface, and on which a waste container may be mounted, said sheet further having an opening whose outline approximates the nominal diameter of the ostomate's stoma and disposed within and adjacent to the inner bounds of said flange, and waste management is attained through the additional use of an insert which includes a relatively rigid, central planar portion with a central opening having an outline approximating, but larger than the outline of the wafer flange, said planar portion, peripherally of said central opening, having a thickness less than the height of said flange, said planar portion having a lateral extend approximating that of the inner surface of said frame, and said frame and said insert having means for preventing relative lateral movement therebetween when the frame is in engagement with the outer surface of the insert, and including the further step of interposing said insert between the frame and the ostomate's torso, with the insert opening telescoped over the wafer flange.

whereby when the belt means are tensioned, the peristomal region of the ostomate is stabilized, with the stabilization pressure spread over the substantial area of the planar portion of the insert lying within the outline of the frame opening, with a concentration of pressure on the adhesive layer of the wafer, peripherally of the ostomate's stoma, and further with the immediate peripheral region of the stoma being stabilized so that there is a minimum of relative movement which would deteriorate the effectiveness of the seal when the flange is subjected to inward and outward pressures incident to attachment and removal of the waste container.

2. A method as in claim 1 wherein the steps of positioning the frame, tensioning the belt means and adhering the sanitary wafer are performed in that order and then the belt means are loosened and the insert is so interposed, and the belt means are retensioned with the frame opening again registered with the ostomate's stoma.

3. A method of body waste management, for ostomates, through the use of a device comprising a relatively rigid frame having a central opening therein, which opening has a span substantially greater than the nominal diameter of the ostomate's stoma, and belt means attached to opposite sides of the frame, at points spaced from the inner surface thereof, said method being particularly adapted to ostomates who, through dietary control, have a minimal liquid content in their faces, and comprising the steps of positioning a pad of absorbent material against the ostomate's stoma and peristomal skin surface, said absorbent pad having portions with a span greater than the frame opening, positioning said frame on the torso of the ostomate, with the opening thereof registered with the ostomate's stoma, and in engagement with said portions of the absorbent pad, securing the belt means about the ostomate's torso with sufficient tension to draw the frame inwardly and stabilize the ostomate's peristomal region disposed generally within the outline of said opening and maintaining the absorbent pad in engagement therewith, and manually removing accumulated, solid feces through use of said adsorbent pad, and placing a barrier sheet of greater outline than the frame against the absorbent prior to stabilization of the peristomal region by the frame.

4. A method of body waste management, for ostomates, through the use of a device comprising a relatively rigid frame having a central opening therein, which opening has a span substantially greater than the nominal diameter of the ostomate's stoma, and belt means attached to opposite sides of the frame, at points spaced from the inner surface thereof, said method being particularly adapted to ostomates who, through dietary control, have a minimal liquid content in their feces, and comprising the steps of positioning a pad of absorbent material against the ostomate's stoma and peristomal skin surface, said absorbent pad having portions with a span greater than the frame opening, positioning said frame on the torso of the ostomate, with the opening thereof registered with the ostomate's stoma, and in engagement with said portions of the absorbent pad, securing the belt means about the ostomate's torso with sufficient tension to draw the frame inwardly and stabilize the ostomate's peristomal region disposed generally within the outline of said opening and maintaining the absorbent pad in engagement therewith, and manually removing accumulated, solid feces through use of said absorbent pad, and placing a perforated barrier sheet of greater outline than the frame against the absorbent pad, prior to stabilization of the peristomal region by the frame.

5. A combination for use in enhancing the effectiveness of a sanitary wafer which comprises a flexible, impervious sheet having a layer of adhesive on its lower, or inner surface, for its attachment to the peristomal skin surface of an ostomate, said sheet having an opening which closely approximates the outline of the ostomate's stoma, said wafer further comprising a relatively rigid, circular flange, projecting from the upper, or outer, surface of said sheet, the inner diameter of which approximates the outline of said opening, said flange providing means for attachment of a waste disposal container to said sanitary wafer, said combination comprising an insert which includes a relatively rigid, central planar portion with a central opening having a diameter approximating, but larger than the outer diameter of the wafer flange, said planar portion, peripherally of said central opening, having a thickness less than the height of said flange, said planar portion having a lateral extent approximating that of the inner surface of sad frame, and a rigid frame having an opening for registration with the planar portion of said insert, said opening being clear of obstruction, the outline of said frame opening being substantially greater than the outline of said central opening of the insert, belt means attached to opposite sides of the frame, at points spaced outwardly from the inner surface thereof, for securing said frame to the ostomate's torso with said opening registered with the ostomate's stoma, whereby when the belt means are tensioned, the peristomal region of the ostomate is stabilized, with the stabilization pressure spread over the substantial area of the planar portion of the insert lying within the outline of the frame opening, with a concentration of pressure on the adhesive layer of the wafer, peripherally of the ostomate's stoma, and further with the immediate peripheral region of the of the stoma being stabilized so that there is a minimum of relative movement which would deteriorate the effectiveness of the adhesive seal when the flange is subjected to inward and outward pressures incident to attachment and removal of a disposal container.

6. A combination as in claim 5 wherein
the insert and frame have means for preventing relative lateral movement therebetween when the frame is held against the insert by the belt means.

7. A combination as in claim 6 wherein
the frame has a circular outline and the lower inner surface thereof is convexly curved, and
the insert includes an outwardly curved flange, into which the lower inner surface of the frame nests, to provide the means for preventing lateral movement.

8. A combination as in claim 5 wherein
the insert has a plurality of openings through through said planar portion, within the outline of said frame opening.
whereby, upon tensioning of the belt means, portions of the ostomate's flesh will protrude through these openings, such protruding portions providing means preventing the insert and frame from shifting laterally relative to the ostomate's torso, as well as providing lines of pressure concentration on the adhesive which deter shifting of the sanitary wafer relative to the ostomate's skin surface.

9. A combination as in claim 8 wherein
the frame opening has a "rounded square" outline at its inner end, and
the openings in the planar portion of the insert take the form of angularly spaced, arcuate slots, concentric of the central opening through which the wafer flange extends.

10. For use in combination with a santiary wafer comprising a flexible, impervious sheet having a layer of adhesive on its lower, or inner surface, for its attachment to the peristomal skin surface of an ostomate, said sheet having an opening which closely approximates the outline of the ostomate's stoma, said wafer further comprising a relatively rigid, circular flange, projecting from the upper, or outer, surface of said sheet, the inner diameter of which approximates the outline of said opening, said flange providing means for attachment of a waste disposal container to said sanitary wafer,
a rigid frame having an opening, said opening being clear of obstruction outwardly of the frame, the outline of said frame opening being substantially greater than said wafer flange,
said frame further having an integral planar portion extending across the bottom or inner end of said frame opening, and having a central opening, having a diameter approximating but slightly larger than the outer diameter of said flange, the thickness of said planar portion, peripherally of said central opening, being less than the height of the wafer flange, and
belt means attached to opposite sides of the frame, at points spaced outwardly from the inner surface thereof, for securing said frame to the ostomate's torso with said opening registered with the ostomate's stoma.
whereby, when the belt means are tensioned, the peristomal region of the ostomate is stabilized, with the stabilization pressure spread over the substantial area of said planar portion, with a concentration of pressure on the adhesive layer of the wafer, peripherally of the ostomate's stoma, and further with the immediate peripheral region of the of the stoma being stabilized so that there is a minimum of relative movement which would deteriorate the effectiveness of the seal when the flange is subjected to inward and outward pressures incident to attachment and removal of a disposal container.

11. A device as in claim 10 wherein
said planar portion has openings therethrough, said openings being disposed within the outline of the inner end of said frame opening,
whereby, upon tensioning of the belt means, portions of the ostomate's flesh will protrude through these openings, such protruding portions providing means preventing the insert and frame from shifting laterally relative to the ostomate's torso, as well as providing lines of pressure concentration on the adhesive which deter shifting of the sanitary wafer relative to the ostomate's skin surface.

12. A device as in claim 11 wherein
the frame has a circular outline and the frame opening has a "rounded square" outline at its inner end, and
the outer bounds of the openings through the planar portion are defined by the corners of the inner end of the frame opening and the inner bounds of these openings are spaced from and concentric with the central opening through which the wafer flange extends.

13. A device as in claim 12 wherein
bridges and connecting posts are formed integrally with the frame, said bridge being spaced outwardly from the outer end of the frame opening and generally outwardly of the outer surface of the frame, and
said belt means include belt portions provided with loops by which they are respectively secured to the bridges.

14. An ostomy device for stablizing the flesh of an ostomate, peristomally of the ostomate's stome,
said device comprising a relatively rigid frame having a central opening terminating in a lip at the inner surface of the frame, the wall of said opening being angled outwardly from said lip to the outer surface of said frame,
said device being unobstructed from the inner end of said opening to the outer surface of the frame,
belt means attached to opposite sides of the frame, at points spaced outwardly from the inner surface thereof, for securing said frame to the ostomate's torso with said opening registered with the ostomate's stoma,
characterized in that
the inner, flesh engaging surface of the frame extends generally normal to said opening, peripherally of said lip and then curves outwardly towards the outer surface of the frame, whereby the belt means may be tensioned to draw the frame into the flesh of the ostomate to stabilize the peristomal region of flesh within the outline of said opening, without discomfort to the ostomate, and
the minimum span across the inner end of said opening is between about 2 and 4 times the nominal diameter of the ostomate's stoma, whereby the stabilized region will be sufficiently large for body waste management and yet sufficiently firm for such purpose, and the thickness of said frame, from its inner surface to its outer surface, is between about 15% and 25% of the minimum span of said opening at its inner end, further characterized in that the frame has bridges at its opposite sides which are supprted by posts in spaced relation from the outer surface of the frame, and the belt means include belt portions provided with loops by which they are respectively secured to the bridges.

* * * * *